United States Patent
Lee et al.

(10) Patent No.: US 9,107,854 B2
(45) Date of Patent: Aug. 18, 2015

(54) EMULSIFIED MQ RESIN: COMPOSITIONS AND METHODS

(75) Inventors: Wilson A. Lee, Hauppauge, NY (US); Geoffrey Hawkins, Yardley, PA (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 13/463,009

(22) Filed: May 3, 2012

(65) Prior Publication Data
US 2013/0295028 A1     Nov. 7, 2013

(51) Int. Cl.
| | |
|---|---|
| *A61K 8/891* | (2006.01) |
| *A61K 8/06* | (2006.01) |
| *A61Q 17/04* | (2006.01) |
| *A61Q 1/02* | (2006.01) |
| *A61Q 5/00* | (2006.01) |
| *A61Q 19/08* | (2006.01) |
| *A61K 8/36* | (2006.01) |
| *A61K 8/60* | (2006.01) |
| *A61K 8/893* | (2006.01) |

(52) U.S. Cl.
CPC .................. *A61K 8/891* (2013.01); *A61K 8/062* (2013.01); *A61K 8/361* (2013.01); *A61K 8/60* (2013.01); *A61K 8/893* (2013.01); *A61Q 1/02* (2013.01); *A61Q 5/002* (2013.01); *A61Q 17/04* (2013.01); *A61Q 19/08* (2013.01); *A61K 2800/594* (2013.01)

(58) Field of Classification Search
CPC .............................. A61K 8/891; A61Q 5/002
See application file for complete search history.

(56) References Cited

U.S. PATENT DOCUMENTS

| | | | |
|---|---|---|---|
| 4,788,001 A | 11/1988 | Narula et al. | |
| 5,112,886 A * | 5/1992 | Phalangas | ...................... 523/332 |
| 5,959,009 A | 9/1999 | Kopnik et al. | |
| 6,180,117 B1 | 1/2001 | Berthiaume et al. | |
| 7,166,276 B2 | 1/2007 | Tephens et al. | |
| 2008/0024744 A1 | 10/2008 | Banes et al. | |

FOREIGN PATENT DOCUMENTS

WO    WO 2010129316 A2 * 11/2010

OTHER PUBLICATIONS

C.R. Robbins. Chemical and Physical Behavior of Human Hair. Feb. 2012. Springer. pp. 346-347.*
Khyat, A.E., Mavon, A., Leduc, M., Agache, P. and Humbert, P. (May 1996); Skin critical surface tension; Skin Research and Technology, vol. 2, Issue 2: pp. 91-96. doi: 10.1111/j.1600-0846.1996.tb00066.x.
Dow Corning; MQ-1600 Solid Resin; Product Information; Personal Care, Sep. 20, 2011; Form No. 27-1382A-01; dowcorning.com.
International Search Report of ISA (KIPO) for PCT application US2013/020145; Mailed Apr. 26, 2013.
Written Opinion of ISA (KIPO) for PCT Application US2013/020145; Mailed Apr. 26, 2013.

* cited by examiner

*Primary Examiner* — Ileana Popa
*Assistant Examiner* — Nicole Babson
(74) *Attorney, Agent, or Firm* — Peter Giancana

(57) ABSTRACT

Long term stable, oil-in-water emulsions that have a high concentration of plasticized MQ-type resin and/or its derivatives in an internal phase. Also, novel compositions for topical use that comprise our MQ resin emulsions. These compositions include, hair care products, especially for treating split ends, skin care products, such as sunscreens, and systems for delivering actives to skin and hair. In some preferred embodiments, the MQ emulsion is stabilized in such a way that the surface tension of the emulsion is sufficiently close to the surface tension of a target surface, such as damaged hair or skin.

14 Claims, 1 Drawing Sheet

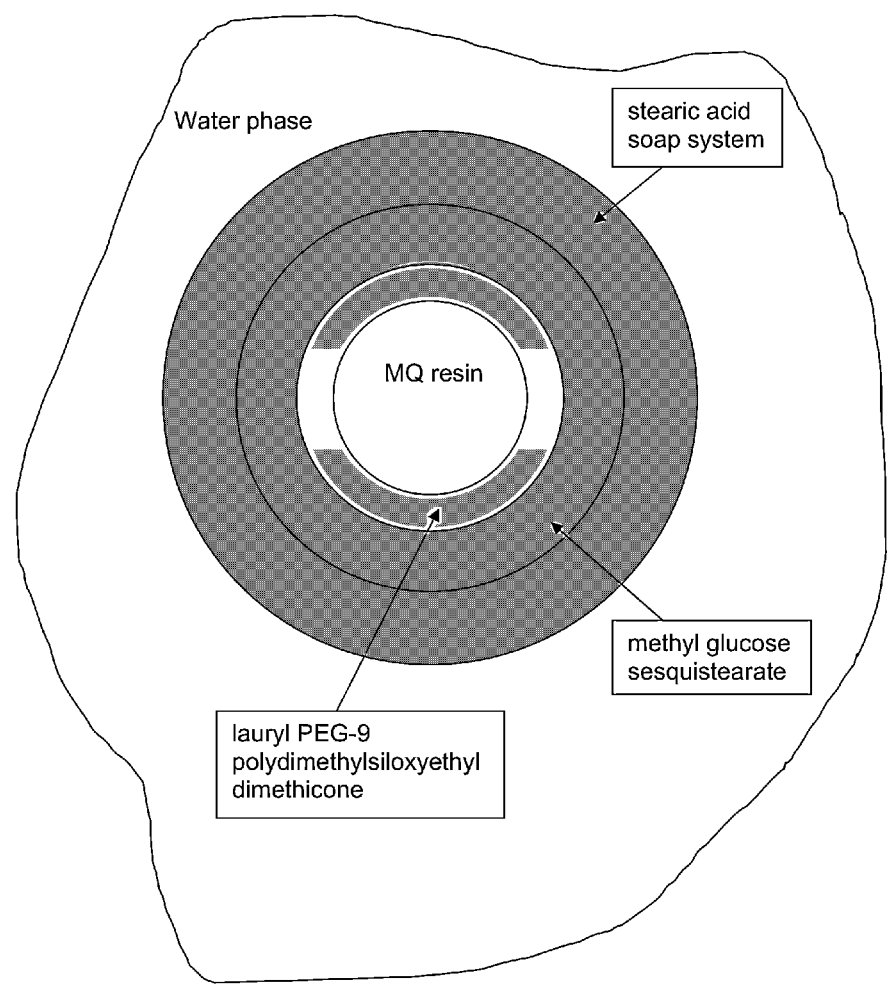

EMULSIFIED MQ RESIN: COMPOSITIONS AND METHODS

FIELD OF THE INVENTION

The present invention pertains to stable emulsions of silicone resin. In particular, the invention pertains to emulsified MQ-type silicone resins. The invention also pertains to compositions comprising emulsified MQ resin, and methods of making such compositions.

BACKGROUND OF THE INVENTION

Trimethylsiloxysilicate is an MQ-type silicone resin that has found assorted uses in personal care products. Two commercially available MQ resins are Silicone SR 1000, from Momentive Performance Materials, and MQ-1600 from Dow Corning. According to some suppliers, trimethylsiloxysilicate may be dissolved in different organic and silicone oils up to concentrations of 50% or more, and is compatible with various types of personal care ingredients, including certain silicones, alcohols, esters and hydrocarbons. The material is hydrophobic, having a reported water contact angle of about 105.8° at standard temperature and pressure. This ingredient offers strong cohesion that may be used to confer transfer resistance and wash-off resistance. The material has film forming and sebum absorption capabilities, and has been used to improve sunscreen products. As a viscosity enhancer, trimethylsiloxysilicate resin has been used to improve the stability of lipsticks and emulsions.

Nevertheless, one significant drawback of pure trimethylsiloxysilicate resin is the difficulty of incorporating the resin into an internal phase of oil and water emulsion systems. Emulsification of up to 3% resin may have been achieved to date, but, to the best of our knowledge, nothing like the much higher concentrations (i.e. 10% to 45% or more) described herein, and especially in systems that are long term stable and suitable for topical application. To the best of the applicant's knowledge, no such emulsion systems existed prior to the present invention.

Another drawback of the material is the brittleness of the film that is formed. If the film is deposited on a non-rigid surface that is subject to change shape (i.e. hair, face, hands, etc.), then the film is likely to crack, flake or peel, thereby compromising product efficacy and providing a user with a poor aesthetic experience.

The ability of a liquid to spread over a surface is governed by relative surface energies. More wetting and more adhesion are achieved when the difference between the surface energies of the two phases are nearly identical. On the other hand, the larger the surface tension of the liquid compared to the surface energy of the solid, the less wetting that occurs. The surface of healthy human hair is coated with fatty acid lipid, making it negatively charged and hydrophobic. Surface energies of healthy hair have been reported to be about 24-28 dynes/cm, while the surface tension of water at 25° C. is about 72 dynes/cm. As a result, the contact angle between healthy hair and water has been reported to be about 103°±4°, with Asian and African hair averaging slightly less than Caucasian hair. Thus, healthy hair is designed to repel water.

In contrast, it is well known that the shaft of the hair may become damaged as a result of over-exposure to chemical agents (as in style and color treatments), mechanical stress (i.e. from combing) and heat (i.e. from blow drying and curling irons). Such overexposure may compromise the protective cuticle layer of the hair fiber, exposing the cortex to further damage. The damage may manifest as a split in the hair shaft that extends from the free end of the hair fiber back toward the scalp. The surface energy of damaged hair may be taken to be about 30-50 dynes/cm, compared to 24-28 dynes/cm for more healthy hair. As a result, damaged hair is significantly less hydrophobic than healthy hair. In fact, many commercial treatments are so harmful, that the hair is rendered somewhat hydrophilic (i.e. water-hair contact angles of 50°-80° have been reported).

A commercially available product line called Nexxus ProMend, from Alberto-Culver, is reported to bind split ends. The products use a polymer solution complex of Polyquaternium 28 (a copolymer of vinylpyrolidone and methacrylaminopropyl trimethylammonium chloride) and PVM/MA copolymer (a copolymer of methyl vinyl ether and maleic anhydride). Our testing showed that after one rinse, Nexxus ProMend products retained only 30 to 60% mending of split ends. To the best of our knowledge, no commercially available product retains at least 75% mending after a minimum of three rinses.

SUMMARY OF THE INVENTION

One aspect of the present invention is a long term stable, emulsion that has an aqueous external or continuous phase and a relatively high concentration of MQ-type resin and/or its derivatives in an internal or discontinuous phase. We refer to these types of emulsions as MQ resin emulsions or simply as MQ emulsions. According to the present invention, MQ emulsions are prepared with a carefully chosen surfactant system. After much research, we have found surfactant systems and methods for incorporating MQ resin and/or derivatives thereof into the internal phase of oil-in-water emulsions. The surfactant system comprises ionic and non-ionic components, as described herein.

We have further discovered novel compositions for topical use that comprise our MQ resin emulsions. These compositions include, but are not limited to hair care products, especially for treating split ends, skin care products, such as sunscreens, and systems for delivering actives to skin and hair.

In some preferred embodiments the MQ resin is plasticized prior to being dispersed in an internal phase of an oil-in-water emulsion. Useful degrees of plasticizing are defined herein.

In some preferred embodiments, care must be taken to ensure that the MQ emulsion is stabilized in such a way that the surface tension of the emulsion is sufficiently close to the surface tension of a target surface, such as damaged hair or skin.

BRIEF DESCRIPTION OF THE DRAWING

The lone FIGURE depicts the layers of an MQ resin emulsion according to the present invention.

DETAILED DESCRIPTION OF THE INVENTION

Definitions Applied Throughout the Specification

"Comprise" and its related conjugates imply that a group is not limited to the members explicitly recited, but may or may not include additional members as well.

By "pure" MQ resin we mean branched, highly crosslinked, water-insoluble networks built solely from monomeric units of $Me_3SiO$ (M unit) and $SiO_4$ (Q unit). In referring to "derivatives" of MQ resin, we mean pure MQ resin that has been altered by replacing a non-critical number of methyl groups and/or a non-critical number of oxygen atoms with one or more substituents. Substituents may be reactive or non-reactive. In general, in choosing derivatives for use in the present invention, substitutents that have lower reactivity will be preferred over substitutents with greater reactivity. By "non-critical number" we mean a degree of substitution that does not significantly deteriorate the stability of the silicone resin emulsion, or significantly interfere with the intended performance of a commercial product. Substitution of oxygen for one or two methyl groups in an M-type monomeric unit, results in a D-type ($Me_2SiO_2$) or T-type ($MeSiO_3$) silicone resin monomeric unit. Likewise, substitution of methyl for one or two oxygen atoms in an Q-type monomeric unit results in a D-type or T-type silicone resin monomeric unit. Silicone resins built from various combinations of M, Q, D and T monomeric units may also find use in the present invention. Besides MQ resin, emulsions based on MT resins and their derivatives are of particular note, but MQ resin and derivatives thereof are preferred.

Continuous Phase

Compositions of the present invention are oil-in-water emulsions. In some preferred embodiments of the invention, the continuous phase is aqueous, and may comprise from 10% to 70% of the total composition. The exact amount will depend upon the intended application. Generally, the water phase may comprise any aqueous-compatible ingredients, as long as the amount of the ingredient(s) does not significantly disturb the stability of the emulsion, or significantly interfere with the intended performance or benefit of the product. Generally, this means that most known hair and skin beautifying agents, and hair and skin care agents may be used in amounts that have been typical for a given agent. Such ingredients include, but are not limited to those intended to beautify the skin and/or hair, benefit the skin and/or hair, those intended to modify or enhance a consumer's perception of the product, and those intended to maintain the quality and integrity of the product. In general, compositions of the present invention have the potential to enhance or extend the benefits provided by many skin and hair care ingredients, by trapping such ingredients near the surface of the skin and/or hair.

Examples of skin and hair care ingredients that may be appropriate for the aqueous phase include: pigments, pearls and dyes, materials that reflect and/or refract light to alter a person's outward appearance, sunscreen, moisturizer, conditioner, exfoliators, DNA repair actives, hair and/or skin barrier repair agents, anti-dandruff agents, anti-oxidants, anti-static agents, styling agents, shine imparting agents, agents that impart body, hair growth promoters, depilatory agents, proteins and other and biological additives. Wheat protein, jojoba and essential oils are just a few examples of ingredients that may be delivered to hair or skin in a novel way by compositions of the present invention, to enhance the benefits that are already known to be delivered by those ingredients. Ingredients that tend to disrupt or destroy barrier layers of the skin or hair are less preferred in compositions of the present invention, and are preferably avoided altogether.

Examples of ingredients that are intended to modify or enhance a consumer's perception of the product, and which may be appropriate for the aqueous phase include: fragrance, color modifiers, pH adjusters, viscosity modifiers, binders, polymers, bulking agents, film formers, plasticizers, solvents, surfactants, suspending agents, and other well known cosmetic adjuvants that modify perception.

Examples of ingredients that are intended to maintain the quality and integrity of the product, and which may be appropriate for the aqueous phase include: preservatives, emulsion stabilizers, color and odor stabilizers, buffers, chelating agents, light stabilizers, and other well known cosmetic adjuvants that maintain product integrity.

Discontinuous Phase

In some preferred embodiments of the invention, the internal phase of the emulsion composition comprises MQ-type silicone resin and/or derivatives thereof, as defined above. As noted above, MT-type resins and/or derivatives thereof may also find use when employed according to the principles disclosed herein. MT-type resins and/or derivatives thereof may be used alone or in combination with MQ-type resins. In compositions according to the present invention, preferred MQ or MT resins have film forming capability and are soluble in hydrocarbon solvents. A preferred film forming MQ resin is trimethylsiloxysilicate resin that has been plasticized to improve its film forming properties. Proper plasticizing will yield a flexible film that is suitable for application to surfaces that may change shape, such as hair and skin. Preferred methods of preparing plasticized MQ-type silicone resins include preparing the plasticized resin as a sub-phase, as disclosed herein. To prepare the plasticized MQ subphase, first dissolve an amount of MQ resin, such as trimethylsiloxysilicate or derivative thereof, in a volatile solvent, such as a volatile hydrocarbon or volatile silicone solvent. For example, one useful solvent is isododecane. Using a swipe mixer, mix MQ resin in isododecane at room temperature until the solution has a high degree of clarity. Thereafter, add dimethicone silicone gum piecemeal, into the dissolved MQ resin with swipe mixing at room temperature, until the final solution is clear and lump free. If it does not interfere with the plasticizing and incorporation of the subphase into the emulsion, then other ingredients may added to the subphase.

In the emulsions that we will disclose, in which the plasticized MQ resin is located in the discontinuous phase, it has been advantageous to prepare the plasticized MQ subphase with trimethylsiloxysilicate resin at about 10% to about 45% by weight of the subphase and dimethicone silicone gum at about 3% to about 30% by weight of the subphase. If it does not interfere with the plasticizing and incorporation of the subphase into the emulsion, then other ingredients may added to the subphase, and q.s. of the solvent to 100% of the subphase. More generally, for various preferred personal care products, the ratio of trimethylsiloxysilicate resin to dimethicone silicone gum in the MQ subphase may be about 15:1 to 1:1. Preferred ratios depend on the type of product, the desired effect, and the frequency of use. For example, some preferred products (i.e. split end treatment products and color adhesion products like certain lipsticks) will tend to be closer to the 15:1 end of the range, as compared to hair styling products that tend toward the 1:1 end of the range, as compared to moisture barrier skin care products (i.e. moisturizers and lip gloss products) that tend to be somewhere in the middle. But this last statement is only a rough guideline, as there is significant overlap in the ratio of trimethylsiloxysilicate resin to dimethicone silicone gum among the various types of products. In principle, useful compositions may also be made when the ratio of trimethylsiloxysilicate resin to dimethicone silicone gum in the MQ subphase is from about 1:1 to about 1:15.

In terms of a total oil-in-water emulsion composition, the plasticized MQ subphase may typically weigh from about 0.1% to about 60% of the total composition, with preferred amounts depending on the type of composition, the desired effect, and the frequency of use. In general, more MQ resin makes for a heavier, tackier product, which is acceptable in some situations and not acceptable in others. In practice, we have found that for some occasional use treatment products, such as those described below, about 20% to about 60% is useful, while 20% to 50% is also suitable for many applications, with 30% to 50% being preferable, and about 40% to 45% being more preferable. On the other hand, for everyday use products, like shampoo or conditioner, significantly lower concentrations may be appropriate. In practice we have found that subphase concentrations of about 0.1% to about 5% can provide an effective benefit. The exact situation will determine what ranges within 0.1% to 60% are preferred. Following its addition to the main composition, some or substantially all of the volatile solvent may evaporate.

When dispersed in a commercial composition according to the present invention, the discontinuous phase may optionally include any suitable skin or hair benefit agent, any ingredient intended to modify or enhance a consumer's perception of the product, and/or any ingredient intended to maintain the quality and integrity of the product.

Surfactant Systems

The surfactant system of the present invention must confer a degree of stability to the silicone resin emulsion to maintain the plasticized MQ resin in an emulsified state. Acceptable stability is defined as commercially acceptable. For example, in the final product, the MQ resin must remain in an emulsified state, even when exposed to temperatures up to about 45° C., at least through an expiration date that has been advertised to a consumer. Such a date should be at least three months from the date of manufacture, preferably at least six months, more preferably at least one year, most preferably at least two years from the date of manufacture, which is common in personal care products, and which consumers have come to expect. Signs of separation between the continuous and discontinuous phases, visible to the unaided eye within such time limit, constitute instability of the emulsion. One preferred surfactant system for use in the present invention comprises a water soluble soap system, a first non-ionic system, and a second non-ionic system. All three are critical.

Soap System

In general, water soluble soaps include at least one water soluble salt of a fatty acid combined with at least one of ammonia, certain amines, alkanolamines and/or alkali metals (such as sodium or potassium). For example, various $C_8$-$C_{20}$ fatty acids, and mixtures thereof, will be useful. In various embodiments, a preferred soap system comprises sodium stearate, formed in situ from sodium hydroxide and stearic acid, the stearic acid being in a range from about 1% to about 6% by weight of the total composition. The amount of a 30% solution of sodium hydroxide may range from about 0.2% to about 1.5% by weight of the total composition. For solutions of sodium hydroxide other than 30%, this range may be adjusted accordingly to ensure that sufficient sodium stearate is generated.

First Non-Ionic System

The first non-ionic system must be oil soluble. In some preferred embodiments, the non-ionic system comprises lauryl PEG-9 polydimethylsiloxyethyl dimethicone (reported HLB of about 3). This material is commercially available as KF-6038 from Shin-Etsu Chemical. PEG-10 dimethicone (KF-6017) with a reported HLB of about 4.5 may also be useful, either alone or in combination with lauryl PEG-9 polydimethylsiloxyethyl dimethicone, as will other non-ionic emulsifiers. In general, when more MQ resin is used in a composition, a first non-ionic emulsifier of lower HLB value is preferred. When relatively less MQ resin is used in a composition, then a first non-ionic emulsifier of higher HLB value may be adequate or even preferred.

The first non-ionic system comprises about 0.2% to about 10% by weight of the total composition of one or more non-ionic oil soluble emulsifiers, such as lauryl PEG-9 polydimethylsiloxyethyl dimethicone and/or PEG-10 dimethicone; preferably about 0.35% to about 3.0%; more preferably about 0.5% to about 1.0%, while about 0.8% is most preferred.

Second Non-Ionic System

A preferred second non-ionic system comprises one or more sugar fatty acid esters and/or derivatives thereof, that exhibit oil-in-water emulsifying activity. The range of concentration of second non-ionic system by weight of the total composition will be about 0.30% to about 6.0%. A preferred sugar fatty acid ester is methyl glucose sesquistearate and/or derivatives thereof. Sugar fatty acid esters such as methyl glucose sesquistearate, are lipophilic at one end (non-polar hydrocarbon chain) and hydrophilic at the opposite end (sugar ring with multi-hydrophilic hydroxide groups). Methyl glucose sesquistearate is particularly well balanced for the present application, and will often be sufficient by itself, as the second non-ionic system. However, other sugar fatty acid esters may be useful in conjunction with methyl glucose sesquistearate. These include, but are not limited to, sucrose monolaurate, sucrose distearate, glucose palmitate, alkylglucose sesquistearates and alkylglucose palmitates, for instance methylglucose palmitate or ethylglucose palmitate, glyceryl monostearate, glyceryl monoisostearate, glyceryl monomyristate, glyceryl monooleate, diglyceryl monostearate, diglyceryl monoisostearate, glyceryl monolaurate, glyceryl monocaprinate, glyceryl monocaprylate, sorbitan monoisostearate, sorbitan monolaurate, sorbitan monocaprylate, sorbitan monoisooleate, as well as derivatives of such compounds. Such optional compounds must be used in a way that does not interfere with the overall function of the second non-ionic system.

Oil-In-Water Emulsions

In preparing oil-in-water emulsions of the present invention, plasticized MQ resin should be formed as the MQ subphase, substantially as described above. Furthermore, the best results are achieved when the alkali metal phase is added to the composition after the MQ subphase has been incorporated. With the addition of alkali metal, the composition assembles in into a stable emulsion, which is believed to be characterized by FIG. 1. The addition of alkali metal facilitates the formation of droplets of plasticized MQ resin surrounded by the first non-ionic system (i.e. lauryl PEG-9 polydimethylsiloxyethyl dimethicone), which is further surrounded by the second non-ionic system (i.e. methyl glucose sesquistearate), which is stabilized in the aqueous phase by the soap system. In general, oil-in-water emulsions according to the present invention may be assembled as follows.

Add the aqueous phase to a main kettle, mix and heat to about 70° C.

In a support kettle, add the fatty acid of the soap system, along with the first and second non-ionic systems. Mix and heat to about 80° C.

Transfer the contents of the support kettle to the main kettle. Mix and cool to about 50° C.

Add the plasticized MQ subphase to the main kettle. Mix and cool to about 45° C.

Add the alkali metal phase. Mix and cool to ambient temperature.

Other steps may intervene as needed. One example of a composition of the invention, in its essential features, is as follows.

Essential Features

Example 1

| Phase 1 | |
|---|---|
| aqueous phase ingredients | 53.70% |
| Phase 2 | |
| fatty acid | 3.00% |
| sugar fatty acid ester | 2.00% |
| lauryl PEG-9 polydimethylsiloxyethyl dimethicone and/or PEG-10 dimethicone | 0.80% |
| Phase 3 | |
| MQ resin subphase | 40.00% |
| Phase 4 | |
| alkali metal solution 30% | 0.50% |

More typically, compositions of the present invention may look like the following non-limiting example (Example 2):

| Phase 1 | |
|---|---|
| water/actives/product enhancers/preservatives | 10.00-70.00% |
| Phase 2 | |
| stearic acid | 1.00-6.00% |
| methyl glucose sesquistearate | 0.30-6.00% |
| lauryl PEG-9 polydimethylsiloxyethyl dimethicone | 0.20-10.00% |
| actives/product enhancers/preservatives | |
| Phase 3 | |
| MQ subphase | 1.00%-60.00% |
| actives/product enhancers/preservatives | |
| Phase 4 | |
| actives/product enhancers/preservatives | |
| Phase 5 | |
| water/sodium hydroxide 30% | 0.20%-1.50% |

Other phases may be included as needed.

Types of Compositions

The emulsion compositions so far described may be implemented as makeup or treatment products for hair, skin and nails.

Hair and Scalp Products

As noted above, the surface energy of healthy hair is about 24-28 dynes/cm, while that of damaged hair has been reported to be about 30-50 dynes/cm. Broadly then, we can say that compositions f the invention mat be applied to hair having a surface tension from about 20 to about 50 dynes/cm. Pure water at 25° C. has a surface tension of about 72 dynes/cm. Therefore, the surfactant system was designed to enable emulsion compositions to have a surface tension that is efficaciously close to the surface energy of the hair being treated. In general, benefits of the emulsion compositions disclosed herein will be realized when the surface tension of the composition is within about 30% of the surface energy of the hair being treated; within 20% is even better; preferably within 10%; more preferably within 5%; and most preferably within 2% of the surface energy of the hair being treated. In general, hair treatment compositions of the invention will have a surface tension from about 14 to about 65 dynes/cm, 16 to 60 is even better, preferably 18 to 55, more preferably 19-52.5; and most preferably 19.6 to 51 dynes/cm, in particular about 30 to about 50 dynes/cm.

Finding surfactant systems that are able to yield an emulsion with the required surface tension, while being commercially stable, and compatible with the plasticized MQ resin, was neither trivial, nor obvious. Nevertheless, the surfactant system described above is useful to make emulsions of this type. Furthermore, the surfactant system described above is such that the surface tension of the final emulsion composition is sensitive to the amount of water in the composition. The degree of sensitivity is such that the easiest way of fine tuning the surface tension of the final composition may be to adjust the amount of water in the composition. This is a real advantage when designing a composition to have a target surface tension.

A composition according to the present invention that is intended for the hair may comprise any ingredients that benefit the hair and/or scalp in the long or short term, as long as the amount of the ingredients does not significantly disturb the stability of the emulsion, nor significantly interfere with the intended benefits of the composition. Particularly of interest are hair benefit molecules of less than about 1,000 Daltons, preferably less that about 750 Daltons, more preferably less that about 500 Daltons, when penetration into the hair cortex is desired. Proteins, such as wheat protein are especially beneficial. Ingredients that hydrolyze the hair, and/or strengthen cystine bonds may be used in the present invention. Various useful actives and hair benefit agents may be apparent to one skilled in the art. Colorants, such as pigments, may also be useful.

When applied to the hair, the external phase of an emulsion of the present invention has an affinity for the hair to which it is closely matched in terms of surface energy. Thus, a layer of aqueous phase tends to form over and around the hair. At the same time, the act of applying the emulsion to the hair causes the emulsion to break along the hair, allowing the plasticized MQ resin droplets to coalesce. The flexibility of the plasticized MQ resin allows the resin to coalesce into a hydrophobic film that sits on top of and surrounds the aqueous layer without cracking. The film is sufficiently strong that the aqueous phase ingredients, such as hair care actives, are trapped near the hair shaft. The film is sufficiently strong to hold the actives in place through multiple wash, blow dry and styling cycles, and to confer added break strength and lubricity to the hair. MQ resins also have the benefit of increasing the shine of the hair.

Compositions for Treating Split Ends

A very interesting commercial application of the present invention is as a composition for treating split ends in hair. A split end composition according to the present invention comprises an oil-in-water emulsion whose surface tension has been adjusted to be substantially close to that of damaged hair. It was unexpected and non-trivial that an emulsion could be stabilized and adjusted for surface tension simultaneously, in a way that would yield a commercially acceptable product that repairs split ends, and that lasts through several wash and rinse cycles, but this is what the applicant has done.

As noted above, the composition may comprise any ingredients as long as the amount of the ingredient does not significantly disturb the stability of the emulsion, or significantly interfere with the ability of the product to repair split ends. Ingredients that when added to a composition of the present invention are able to disrupt layers of the hair cuticle in ways that promote split ends are less preferred in compositions of the present invention, and are preferably avoided altogether. In preferred embodiments of a split end treatment composition, the plasticized MQ resin subphase tends to have relatively higher concentrations of trimethylsiloxysilicate resin. That is, the ratio of trimethylsiloxysilicate resin to dimethicone silicone gum in the MQ subphase tends toward the 15:1 end of the range given above. One example of an effective composition for treating split ends is as follows.

Split End Treatment Product

Example 3

| water | 45.90% |
|---|---|
| hydrolyzed wheat protein | 0.50% |
| xanthan gum | 0.40% |
| butylene glycol | 1.00% |
| preservatives | 0.55% |
| stearic acid | 3.00% |
| methyl glucose sesquistearate | 2.00% |
| lauryl PEG-9 polydimethylsiloxyethyl dimethicone | 0.80% |
| cholesterol (for barrier repair) | 0.40% |
| vitamin E | 0.05% |
| cetearyl alcohol/cetearyl glucoside (thickener) | 1.50% |
| glyceryl stearate citrate | 0.80% |
| preservatives | 0.80% |
| MQ subphase | 40.00% |
| (isododecane) | (52.00%) |
| (trimethylsiloxysilicate) | (35.50%) |
| (silicone gum) | (12.50%) |
| dimethicone fluid | 1.00% |
| preservative | 0.80% |
| water/sodium hydroxide 30% | 0.50% |

The surface tension of this emulsion was measured to be 33.5 dynes/cm, at room temperature. Thus, the emulsion will display a high degree of affinity for damaged hair. When applied to the hair, the emulsion has an affinity for the damaged hair to which it is closely matched in terms of surface energy. Thus, a layer of aqueous phase tends to form over and around the hair, near the site of damage, that is, along the split ends. At the same time, the act of applying the emulsion to the hair causes the emulsion to break, allowing the plasticized MQ resin droplets to coalesce. The flexibility of the plasticized MQ resin allows the resin to coalesce into a hydrophobic film that sits on top of and surrounds the aqueous layer without cracking. The strong cohesiveness of the MQ resin draws the split ends together, and the aqueous phase ingredients, such as hair care actives, are trapped near to the exposed cortex. The film cohesion is sufficient to maintain the split end repair through multiple wash, blow dry and styling cycles, and to confer added break strength and lubricity to the hair. MQ resins also have the benefit of increasing the shine of the hair. The benefit of spit end repair alone, and all the aforementioned benefits as a whole, are unexpectedly superior to other hair care or split end treatment products on the market.

The hair products so far described may be applied to dry or wet hair and worked through the hair by combing, or with the fingers, or by other means. The high concentration of silicone resin allows the resin to remain in the hair for several wash and rinse cycles, so that the treatment may not need to be applied everyday. For example, methods of treating split ends in hair may comprise occasionally applying compositions of the invention to the hair only occasionally, such as every other day, or every third day, or twice per week, or once per week while still providing significant split end treatment. We evaluated split end treatment as follows.

A composition according to Example 3 was prepared. A tress of hair having fibers damaged with split ends was obtained. Within each tress, 20 split end fibers were randomly tagged for tracking. The hair was washed and rinsed with shampoo (Pantene Classic) and water, in the conventional manner of shampoo cleansing. Subsequently, the hair was towel dried. Thereafter, a dime-sized amount (about 0.5 grams) of the composition was applied through out the tress of damp hair with the fingers. Following this initial application the condition of the tagged fibers was noted by microscopy. The tress was then washed and rinsed with shampoo (Pantene Classic) and water, in the conventional manner of shampoo cleansing. After rinsing, the tresses were blown dry. Then, each tress received two passes with a hot iron, subjecting the hair fibers to temperatures of approximately 425° F. This wash, blow dry, hot iron cycle was repeated multiple times, and the condition of the tagged fibers within the tress was noted throughout, by microscopy.

Immediately following treatment, 100% of the split end fibers were mended. Following a fourth wash/dry/hot iron cycle, 75% (15/20) of split ends were still mended. Following a fifth cycle, 80% (16/20) of split ends were mended. Following a sixth cycle, 75% (15/20) of split ends were still mended. Thus, the MQ resin emulsion of the present invention provided very effective treatment for split ends, the benefits of which remained in the hair even after 6 wash/blow dry/hot iron cycles, without reapplication of the MQ emulsion composition. The film forming abilities of this composition and its substantivity for damaged hair, provide a long lasting split end treatment.

Another use of emulsion compositions according to the present invention, and a major advantage of the present invention, is the ability to disperse a fully assembled MQ resin emulsion composition according to the present invention into an aqueous system, such as shampoo or conditioner or all-in-one shampoo and conditioner. By so doing, any suitable aqueous product may be transformed by incorporating the benefits of the MQ emulsion. For example, by dispersing the composition of Example 3 into a shampoo (or other product suitable for applying to the hair), the shampoo is transformed into a split end treatment product. In general, the concentration of MQ resin will be significantly lower in the new product than in the original emulsion. Nevertheless, hair care benefits like split end repair are still achieved. However, due to the lower concentration, the treatment must be repeated more often than occasionally to maintain the benefit. But this is not a substantial disadvantage for products like shampoo or conditioner, which may be used at least once per day. An overriding concern is that the amount of emulsion dispersed should not significantly interfere with the foaming, lathering, cleaning or conditioning properties of the host composition. We have found that a silicone emulsion according to our invention may typically comprise about 0.1% to 3.0% of the shampoo or conditioner composition, without adversely affecting properties of the host composition, such as foaming, lathering, cleaning and conditioning. We evaluated split end treatment as follows.

As host compositions, we used Damage Reverse Restorative Shampoo and Damage Reverse Restorative Conditioner from Aveda. At room temperature, an MQ resin emulsion in accordance with Example 3 (40% MQ subphase) was dispersed into each of these finished commercial products at a concentration of 1%. Thus, the modified shampoo and conditioner comprised about 0.40% MQ subphase. Thereafter, 0.1-0.2 grams of shampoo was applied to one tress of hair, and 0.1-0.2 grams of conditioner was applied to another tress of hair. The hair in each tress was damaged with split ends. Within each tress, 20 split end fibers were randomly tagged for tracking.

The shampoo and conditioner were applied to each tress with water, in the conventional manner of shampoo and conditioner to wash and rinse the hair. After rinsing, the tresses were blown dry. Then, each tress received two passes with a hot iron, subjecting the hair fibers to temperatures of approximately 425° F. This wash/blow dry/hot iron cycle was repeated multiple times, and the condition of certain fibers within each tress was noted throughout. Following each cycle, the condition of the tagged fibers was noted by microscopy. Following a first cycle with the shampoo product, 90% (18/20) of split ends were mended. Following a second cycle, 90% (18/20) of split ends were mended. Following a first cycle with the conditioner, 95% (19/20) of split ends were mended. Following a second cycle, 90% (18/20) of split ends were mended. Thus, even when the MQ subphase is dispersed at 0.4% into another product, the MQ resin emulsions of the present invention may provide very effective treatment for split ends. For example, methods of treating split ends in hair may comprise applying compositions of the invention to the hair at least daily, such as once per day or twice per day or more frequently. Although we have demonstrated this with a shampoo and conditioner, MQ resin emulsions of the present invention may be dispersed as described into other hair care or skincare products.

Skin Care Products

Human skin is generally hydrophobic. Surface tension of skin varies depending on the type and condition of the skin, the location on the body, and how recently it has been cleaned. For example, reported skin surface tension values include 27.5±2.4 dyne/cm on the volar forearm, and over 50.7 dyne/cm on the forehead. However, after cleansing with ether, these reduced to 21.6±2.6 dyne/cm and 29.3±1.7 dyne/cm. After washing with soap and water, the forearm surface tension reduced to 23.7±1.0 dyne/cm. (see A. El Khyat, et al., "Skin critical surface tension," Skin Research and Technology vol. 2, issue 2, p. 91-96; May 1996.) Thus, emulsion compositions according to the present invention may be formulated to have surface tension substantially close to that of human skin. Once the emulsion breaks across the skin, a film of MQ resin, covering an aqueous layer forms over the treated area. The silicone film traps water and skin benefit agents near the skin surface. Evaporation of skin-bound water is hindered by the MQ resin film. Thus, emulsions according to the present invention are well suited as moisturizers, skin active delivery systems, wear resistant systems, etc.

A composition according to the present invention that is intended for the skin may comprises any ingredients that benefit the skin in the long or short term, as long as the amount of the ingredients does not significantly disturb the stability of the emulsion, or significantly interfere with the intended benefits of the composition. These agents may be dispersed as appropriate, in the external or internal phase of the MQ emulsion, but it is expected that water soluble ingredients are particularly beneficial because of the aqueous layer that becomes trapped next to the skin. Any of the many skin benefit agents that are well known in the fields of cosmetics and dermatology may find use in these skin care compositions, such as in the following.

Anti-Wrinkle Product

Example 4

| Phase 1 | |
|---|---|
| water | 48.30% |
| tetrapeptide-21 (and) glycerin (and) butylene glycol (and) water | 2.10% |
| glycerin | 2.10% |

-continued

| Phase 2 | |
|---|---|
| polyglyceryl-3 methylglucose distearate | 2.10% |
| glyceryl stearate | 1.40% |
| stearyl alcohol | 0.70% |
| caprylic/capric triglyceride | 6.60% |
| C12-15 alkyl benzoate | 6.60% |
| Phase 3 | |
| stearic acid | 3.00% |
| methyl glucose sesquistearate | 2.00% |
| PEG-10 dimethicone | 0.80% |
| Phase 4 | |
| MQ subphase | 22.7% |
| (isododecane) | (50.00%) |
| (trimethylsiloxysilicate) | (33.00%) |
| (silicone gum) | (17.00%) |
| dimethicone liquid | 1.00% |
| Phase 5 | |
| preservative qs | |
| fragrance qs | |
| Phase 6 | |
| water/sodium hydroxide 30% | 0.50% |

Note:
phases 1 and 2 should be separately combined and heated to 70-75° C., prior to combining with stirring and homogenizing.

Of particular interest are sunscreen compositions, especially those employing sunscreen agents in an aqueous phase. Sunscreen agents may include organic compounds that absorb ultraviolet light, and inorganic particulates that scatter and/or absorb UV light. Any of the following sunscreen agents may be useful alone or in combination: avobenzone, bisdisulizole disodium, diethylamino hydroxybenzoyl hexyl benzoate, ecamsule, methyl anthranilate, 4-aminobenzoic acid, cinoxate, ethylhexyl triazone, homosalate, 4-methylbenzylidene camphor, octyl methoxycinnamate, octyl salicylate, padimate O, phenylbenzimidazole sulfonic acid, polysilicone-15, trolamine salicylate, bemotrizinol, benzophenones 1-12, dioxybenzone, drometrizole trisiloxane, iscotrizinol, octocrylene, oxybenzone sulisobenzone, bisoctrizole, titanium dioxide, and zinc oxide. Preferably, the composition exhibits a sun protection factor of at least 10. Preferably, the composition comprises sunscreen agents that offer protection from one or more of UV-A, UV-B and UV-C radiation. The emulsion compositions according to the present invention may be implemented as wear resistant sunscreen products. Once the emulsion breaks across the skin, a film of MQ resin, covering an aqueous layer forms over the treated area. The silicone film traps aqueous phase sunscreen agents and other actives near the skin surface.

Sunscreen Product

Example 5

| water | 44.50% |
|---|---|
| polyquaternium-37 (and) polyquaternium-37 | 1.00% |
| glycerine | 4.00% |
| Eusolex T 2000[1] | 4.00% |
| silica | 0.5% |
| propylheptyl caprylate | 2.00% |
| cocoglycerides | 2.00% |
| Tinosorb S[2] | 4.00% |
| Eusolex OS[3] | 4.00% |
| Eusolex HMS[4] | 4.00% |
| stearic acid | 3.00% |

-continued

| | |
|---|---|
| methyl glucose sesquistearate | 2.00% |
| lauryl PEG-9 polydimethylsiloxyethyl dimethicone | 0.80% |
| vitamin E | 0.05% |
| preservatives | 1.00% |
| MQ subphase | 20.65% |
| (isododecane) | (50.00%) |
| (trimethylsiloxysilicate) | (45.00%) |
| (silicone gum) | (5.00%) |
| dimethicone liquid | 1.00% |
| preservative | 1.00% |
| water/sodium hydroxide 30% | 0.50% |

[1]Titanium dioxide (and) alumina (and) dimethicone
[2]Bis-ethylhexyloxyphenol methoxyphenyl triazine
[3]Ethylhexyl salicylate
[4]Homosalate Suitable makeup or color cosmetic products for the skin may also be obtained.

Foundation Product

Example 6

| Phase 1 | |
|---|---|
| Water | 45.00% |
| magnesium aluminum silicate | 0.35% |
| butylene glycol | 2.00% |
| sodium carboxyl methylcellulose | 0.30% |
| Phase 2 | |
| Lecithin | 0.20% |
| Triethanolamine | 1.00% |
| Phase 3 | |
| titanium oxide | 8.00% |
| iron oxide red | 0.40% |
| iron oxide yellow | 0.80% |
| iron oxide black | 0.10% |
| methylparaben | 0.20% |
| calcium aluminum borosilicate | 2.00% |
| Phase 4 | |
| stearic acid | 3.00% |
| methyl glucose sesquistearate | 2.00% |
| lauryl PEG-9 polydimethylsiloxyethyl dimethicone | 0.80% |
| propylparaben | 0.20% |
| Phase 5 | |
| MQ subphase | 28.05% |
| (isododecane) | (52.00%) |
| (trimethylsiloxysilicate) | (36.00%) |
| (silicone gum) | (12.00%) |
| isoeicosane | 5.00% |
| Phase 6 | |
| water/sodium hydroxide 30% | 0.50% |
| Imidazolidinyl urea | 0.10% |

Procedure: Charge water into a main vessel. In a secondary vessel, disperse magnesium aluminum silicate into butylene glycol, then disperse sodium carboxyl methylcellulose and mix until uniform. Add secondary vessel to main vessel with propeller mixing. Mix until uniform. Add Phase 2 and mix until uniform. Add Phase 3 with homogenization. Homogenize until uniform. Begin heating to 72° C. In a support vessel, add the fatty acid of the soap system, along with the first and second non-ionic systems. Mix and heat to about 80° C. Transfer the contents of the support vessel to the main vessel. Mix and cool to about 50° C. Add the plasticized MQ subphase to the main kettle. Mix and cool to about 45° C. Add the alkali metal phase. Mix and cool to ambient temperature.

Another aspect of the invention includes a consumer package that comprises a container that holds a stable emulsion composition according to the invention, and an indication of how often the product should be used to achieve and/or maintain a certain benefit. The indication may be, for example, text printed on a portion of the package. One non-limiting example of this aspect of the invention is a consumer package that comprises a container that holds a stable emulsion product according to the invention, wherein the subphase of the emulsion weighs from about 20% to about 60% of the total product, and an indication that the product should be used at least once per week. Another non-limiting example would be a consumer package that comprises a container that holds a stable emulsion product according to the invention, wherein the subphase of the emulsion weighs from about 0.1% to about 5% of the total product, and an indication that the product should be used at least daily. Such consumer packages will provide enough product for at least one treatment or application according to proscribed or intended use, preferably enough for at least one week's worth of applications, more preferably at least one month's worth of applications according to proscribed or intended use.

What is claimed is:

1. A stable emulsion product comprising:
    a continuous aqueous phase;
    a discontinuous phase emulsified into the continuous phase, comprising:
        a subphase of trimethylsiloxysilicate resin that has been plasticized with dimethicone silicone gum and volatile solvent, wherein the ratio of trimethylsiloxysilicate resin to dimethicone silicone gum in the subphase is about 15:1 to 1:15; and
        a surfactant system comprising: stearic acid and sodium hydroxide; lauryl PEG-9 polydimethylsiloxyethyl dimethicone and optionally PEG-10 dimethicone; and methyl glucose sesquistearate;
        wherein the discontinuous phase of the stable emulsion product is characterized by droplets of plasticized trimethylsiloxysilicate resin surrounded by a layer of lauryl PEG-9 polydimethylsiloxyethyl dimethicone, which is further surrounded by a layer of methyl glucose sesquistearate.

2. The stable emulsion product of claim 1 wherein the ratio of trimethylsiloxysilicate resin to dimethicone silicone gum in the subphase is about 15:1 to 1:1.

3. The stable emulsion product of claim 1 wherein the subphase comprises trimethylsiloxysilicate resin at about 10% to about 45% by weight of the subphase, and dimethicone silicone gum at about 3% to about 30% by weight of the subphase.

4. The stable emulsion product of claim 1 wherein the solvent is isododecane.

5. The stable emulsion product of claim 1 wherein the surface tension of the product is from about 14 to about 65 dynes/cm.

6. The stable emulsion product of claim 5 for treating split ends in hair, wherein the surface tension of the product is from about 30 to about 50 dynes/cm.

7. The stable emulsion product of claim 5 that is a shampoo or conditioner or all-in-one shampoo and conditioner.

8. The stable emulsion product of claim 5 that further comprises at least one skin care ingredient.

9. The stable emulsion product of claim 5 that further comprises one or more sunscreen agents and that exhibits a sun protection factor of at least 10.

10. The stable emulsion product of claim 5 that is a color cosmetic product comprising pigments, pearls, dyes and/or materials that reflect and/or refract light to alter a person's outward appearance.

11. The stable emulsion product of claim 1 wherein the aqueous phase comprises about 10% to about 70% of the total composition, and wherein the subphase comprises about 0.1% to about 60% of the total composition.

12. A package comprising:
a container that holds the stable emulsion product of claim 1, wherein the subphase of the emulsion weighs from about 20% to about 60% of the total product, and
an indication that the product should be used at least once per week.

13. A package comprising:
a container that holds the stable emulsion product of claim 1, wherein the subphase of the emulsion weighs from about 0.1% to about 5% of the total product, and
an indication that the product should be used at least daily.

14. A method of treating hair with split ends comprising the step of applying to the hair with split ends the stable emulsion product of claim 1.

* * * * *